(12) United States Patent
Karami et al.

(10) Patent No.: US 8,562,581 B2
(45) Date of Patent: Oct. 22, 2013

(54) SKIN FRIENDLY DIAPER

(75) Inventors: Hamzeh Karami, Brewster, MA (US);
Babak Damaghi, Kings Point, NY (US)

(73) Assignee: First Quality Products, Inc., State College, PA (US)

( * ) Notice: Subject to any disclaimer, the term of this patent is extended or adjusted under 35 U.S.C. 154(b) by 371 days.

(21) Appl. No.: 10/841,119

(22) Filed: May 7, 2004

(65) Prior Publication Data
US 2005/0261647 A1    Nov. 24, 2005

(51) Int. Cl.
*A61F 13/15*    (2006.01)
(52) U.S. Cl.
USPC .......................... 604/391; 604/386; 604/402
(58) Field of Classification Search
USPC ............ 604/386, 389–391, 395, 385.14, 402
See application file for complete search history.

(56) References Cited

U.S. PATENT DOCUMENTS

| | | | |
|---|---|---|---|
| 2,828,745 A | 4/1958 | Deutz | |
| 3,509,881 A | 5/1970 | Sabee | |
| 4,051,854 A | 10/1977 | Aaron | |
| 4,770,656 A | 9/1988 | Proxmire et al. | |
| 4,808,176 A | 2/1989 | Kielpikowski | |
| 4,834,736 A | 5/1989 | Boland et al. | |
| 4,834,742 A | 5/1989 | Wilson et al. | |
| 4,842,596 A | 6/1989 | Kielpikowski et al. | |
| 5,387,208 A | 2/1995 | Ashton et al. | |
| 5,397,317 A | 3/1995 | Thomas | |
| 5,476,758 A * | 12/1995 | Suga et al. | 430/503 |
| 5,527,300 A | 6/1996 | Sauer | |
| 5,562,648 A | 10/1996 | Peterson | |
| 5,571,096 A | 11/1996 | Dobrin et al. | |
| 5,593,400 A | 1/1997 | O'Leary | |
| 5,595,567 A | 1/1997 | King et al. | |
| 5,601,544 A | 2/1997 | Glaug et al. | |
| 5,628,737 A | 5/1997 | Dobrin et al. | |
| 5,643,239 A | 7/1997 | Bodford et al. | |
| 5,735,840 A | 4/1998 | Kline et al. | |
| 5,797,896 A | 8/1998 | Schmitz | |
| 5,858,515 A | 1/1999 | Stokes et al. | |
| 5,897,547 A | 4/1999 | Schmitz | |
| 5,928,212 A * | 7/1999 | Kline et al. | 604/391 |
| 5,997,981 A | 12/1999 | McCormack et al. | |
| 6,192,556 B1 | 2/2001 | Kikko et al. | |
| 6,193,701 B1 | 2/2001 | Van Gompel et al. | |
| 6,210,389 B1 | 4/2001 | Long et al. | |
| 6,387,085 B1 | 5/2002 | Van Gompel et al. | |
| 6,423,042 B1 | 7/2002 | Sasaki | |
| 6,464,677 B1 * | 10/2002 | Noguchi et al. | 604/385.27 |
| 6,468,257 B1 * | 10/2002 | Ono et al. | 604/391 |
| 6,600,086 B1 | 7/2003 | Mace et al. | |
| 6,663,612 B2 * | 12/2003 | Shingu et al. | 604/391 |
| 6,761,711 B1 * | 7/2004 | Fletcher et al. | 604/389 |
| 2002/0022814 A1 | 2/2002 | Otsubo et al. | |
| 2003/0135185 A1 | 7/2003 | Crowther | |
| 2004/0064126 A1 | 4/2004 | Fletcher et al. | |

* cited by examiner

*Primary Examiner* — Lynne Anderson
(74) *Attorney, Agent, or Firm* — Amster, Rothstein & Ebenstein LLP

(57) ABSTRACT

A disposable absorbent article is disclosed having a wide breathable backsheet formed of a single layer of material, preferably in an hourglass configuration, and a narrow containment assembly attached to the backsheet along its longitudinal axis. The placement of the containment assembly creates two regions on either side of the backsheet which form wings which extend laterally beyond the margins of the containment assembly. Fasteners provided on the wings permit attachment of the wings together to form breathable side panels. The fasteners may be configured to engage limited areas of the backsheet and to resist engagement of other areas thereof. The containment assembly comprises a pervious topsheet and an impervious backing film sandwiching an absorbent core. The backing film is generally as narrow as the top sheet, maximizing the breathable area of the absorbent article, and minimizing the use of environmentally persistent plastic films.

34 Claims, 3 Drawing Sheets

SKIN FRIENDLY DIAPER

FIELD OF THE INVENTION

The present invention relates generally to disposable absorbent garments such as disposable diapers, and more specifically to disposable diapers having skin friendly breathable side panels or "wings" which may act as landing zones for hook-and-loopless fasteners.

BACKGROUND OF THE INVENTION

Infants and other incontinent individuals wear disposable absorbent articles such as diapers to absorb and contain body exudates discharged from the body, particularly urine. Absorbent articles function to contain the discharged materials in isolation from the body of the wearer on one side, and from the wearers garments and/or bedding on the other. Absorbent articles are well known in the art and are typically constructed from a combination of liquid and vapor pervious and impervious materials which respectively allow the passage of liquid into the diaper and prevent its exit therefrom.

It is known to fasten a diaper about the body of a user using a variety of fasteners having a fastening material such as adhesive or a two part hook-and-loop type (i.e. Velcro). These fasteners are typically located at a front or rear portion of the diaper, such as a flap or wing, and are oriented to engage a "landing zone" on an opposing portion of the diaper. For an adhesive fastener, a release strip may be used as a landing zone; a Velcro fastener requires a special looped landing zone.

U.S. Published Patent Application No. US 2003/0004490 A1, issued to Larsson et al. discloses an absorbent article such as a diaper having a landing zone arranged on the front or rear portion of the product and at least one hook-bearing tab arranged on the front or rear portion of the product and at least one hook-bearing tab for detachable interaction with the landing zone. The landing zone includes both active areas, to which the tabs can be fastened, and inactive areas which will not adhere to the tabs. Particularly, the landing zone is a continuous support strip with an inactive area connected between two active areas. This enables two landing zones to be formed in one manufacturing step, from a single strip.

It is also known to make a diaper having Velcro-like hooks as one component of a fastening system and a nonwoven outer surface which serves as the other component. In such a diaper, the hook does not require a special landing zone having special loops. Instead, the entire outer surface of the diaper or brief can function as a landing zone for the hooks. This is known as a "loopless" fastening system, and provides an increased degree of flexibility in the fitting of a diaper to a person. Such a loopless fastener system is described in U.S. Patent Application Publication No. US 2003/0220626 A1 filed on May 7, 2003 and is hereby incorporated by reference.

Although such a loopless fastening system is more convenient for the user, there may be a tendency to take advantage of the unlimited landing area provided by loopless fasteners to use diapers that are not properly sized to the wearer. Particularly, diapers that are too large may still be nominally fitted to an individual due to the ability of the loopless fasteners to gather in the slack created by the oversized diaper. This practice is wasteful as larger diapers are likely to be more expensive, and require more material to manufacture.

U.S. Pat. No. 5,387,208 issued to Ashton et al. on Feb. 7, 1995 discloses an example of a diaper employing a plurality of layers of pervious, absorbent and impervious materials. Particularly, Ashton et al. discloses a pervious body facing top sheet and an impervious garment facing backsheet sandwiching a plurality of layers of variously liquid pervious and absorbent material. The liquid impervious backsheet extends beyond the dimension of the top and intervening layers, thereby providing laterally extending tabs which can be joined about the waist of the wearer to hold the diaper in place during use.

Although such backsheets do prevent liquid from passing through the diaper, the impervious nature of the backsheet, often a polyethylene film, also prevents the passage of air and water vapor, resulting in a diaper which can feel hot and uncomfortable to wear.

Backsheets which are pervious to vapor are generally known as breathable backsheets and have been described in the art. In general, these backsheets are intended to allow the passage of vapor through them while retarding the passage of liquid. For example, U.S. Pat. No. 3,156,242 issued to Crowe, Jr. on Nov. 10, 1964 teaches the use of a microporous film as a breathable backsheet. U.S. Pat. No. 3,881,489 issued to Hartwell on May 6, 1975 teaches a breathable backsheet having two layers, the first of which is a thermoplastic film and the second of which is a hydrophobic tissue.

While perforated backsheets may provide improved breathability over an impervious backsheet, the materials are of limited utility as they may require multiple layers of materials to prevent leakage. Fundamentally, perforation of otherwise impervious films achieves a measure of breathability at the expense of the material's ability to resist the flow of liquid, particularly when a diaper is subjected to the normal forces created by the wearer during use.

A modified approach is disclosed in U.S. Pat. No. 5,628,737 issued to Dobrin et al. on May 13, 1997, which provides a diaper having an impervious backsheet which extends laterally beyond the dimensions of the absorbent core and top sheet on the diaper wherein only the side panels are provided with perforation, thereby providing an impervious region adjacent to the core and a breathable region which permits some movement of vapor therethrough. This approach creates a zone of liquid impermeability where leaks would otherwise be most likely to occur in the backsheet, and provides a breathable region where leaks are less likely, e.g. where the backsheet comes in direct contact with the skin of the wearer.

Although the creation of zones of permeability in a diaper resolves some of the problems which are inherent to the backsheets of the prior art, the perforation of even an isolated region of a plastic film backsheet presents its own shortcomings, particularly due to the inherently impervious character of plastic film. For example, an impervious side panel having relatively large or many perforations may achieve the desired breathability, at the expense of the material strength in the perforated zone. Conversely, side panels having relatively few or small perforations may remain strong, yet provide insufficient breathability to ensure the comfort of the wearer. Basically, the shortcomings of the prior art stem from the attempt to make an impervious material selectively behave like a pervious material. Particularly, when this is attempted on a plastic film, the result cannot be accomplished without undermining the plastic film itself, where increased breathability comes at the expense of the material's desirable properties.

An additional disadvantage of the disposable diapers of the prior art is that extensive use of impervious material, typically plastic films, is environmentally detrimental as these films are known to be non-biodegradable. The introduction of perforations into otherwise impervious films as suggested in the prior art does not render these substances environmentally friendly. The environmental consequences are above and beyond the other economic disadvantages consequences of present diaper designs, particularly that the use of multiple layers of material and the application of the complex manufacturing techniques necessary in current diaper designs render these approaches more costly than necessary to manufacture and therefore less economical to purchase.

Finally, the use of a plastic film as a backsheet precludes the use of a loopless fastener system because a plastic film cannot function as a landing zone for a loopless fastener.

Another approach to creating a disposable absorbent article having breathable side panels is found in the Prevail® version of protective underwear manufactured by First Quality Products, Inc. of McElhattan, Pa. The brief comprises a nonwoven pervious backsheet having an absorbent assembly attached thereto. The product crotch areas are provided with elastic bands sandwiched between the backsheet and an additional layer of nonwoven material. Thus, the side panels are generally pervious, although breathability is impeded by the multiple laminated nonwoven layers, and the adhesive that laminates them. This construction is similar to the Per-Fit® version of diaper, also manufactured by First Quality Products, Inc. which provides increased breathability in side panels comprising two laminated layers of nonwoven material, and is subject to the same drawbacks.

Therefore a need exists for an absorbent article such as a diaper having a fastening system which prevents improper sizing of oversized diapers.

A further need exists for an absorbent article such as a diaper having an absorbent core capable of absorbing and retaining fluids, while maximizing the breathability of the article.

A still further need exists for an absorbent article which minimizes the use of fluid impervious and/or non-biodegradable substances.

SUMMARY OF THE INVENTION

It is therefore a feature of various embodiments of the invention to address the aforementioned needs by providing a disposable absorbent article, such as a diaper, having a liquid and/or vapor pervious backsheet formed of a single ply of material which extends laterally from a narrow fluid containment assembly having a liquid impervious backing film. The lateral extensions of the backsheet form a plurality of wings by which the absorbent article is secured about the body of a wearer, typically an infant.

In accordance with an embodiment of the invention, the diaper is provided with loopless fasteners on one portion thereof, and a nonwoven backsheet which functions as a landing zone for the loopless fasteners. A portion of the backsheet is provided with an area to which the loopless fasteners cannot attach. By controlling the size and location of this "stay-away-zone" improper sizing of diapers can be prevented.

In accordance with another embodiment of the invention, the containment assembly may be comprised of a liquid and vapor pervious topsheet and a liquid and vapor impervious backing film sandwiching an absorbent core to absorb and contain body exudates. The pervious topsheet and impervious backing film have approximately the same dimensions, and are sufficiently sized to completely contain the absorbent core. The dimensions of the containment assembly, particularly those of the impervious backing film and the topsheet, are laterally narrower than the widest dimension of the backsheet to which the containment assembly is attached.

In accordance with still another embodiment of the present invention, the backing film may be formed of multiple layers of material, or may be perforated such as to remain fluid impervious but to become vapor pervious.

Other features and advantages of the present invention will become readily apparent from the following detailed description, the accompanying drawings and the appended claims.

DESCRIPTION OF THE PREFERRED EMBODIMENTS

As used herein, the term "absorbent article" refers to devices which absorb and contain body exudates, and more specifically, refers to devices which are placed against or in proximity to the body of the wearer to absorb and contain the various exudates discharged by the body. The term "disposable" is used herein to describe absorbent articles which are not intended to be laundered or otherwise restored or reused as an absorbent article, but instead are intended to be discarded after a single use and, preferably, to be recycled, composted or otherwise disposed of in an environmentally compatible manner. A "unitary" absorbent article refers to absorbent articles, such as diapers, which are formed of separate parts united together to form a coordinated entity so that they do not have multiple parts or require assembly prior to use such as a separate holder and liner.

Figure 1:
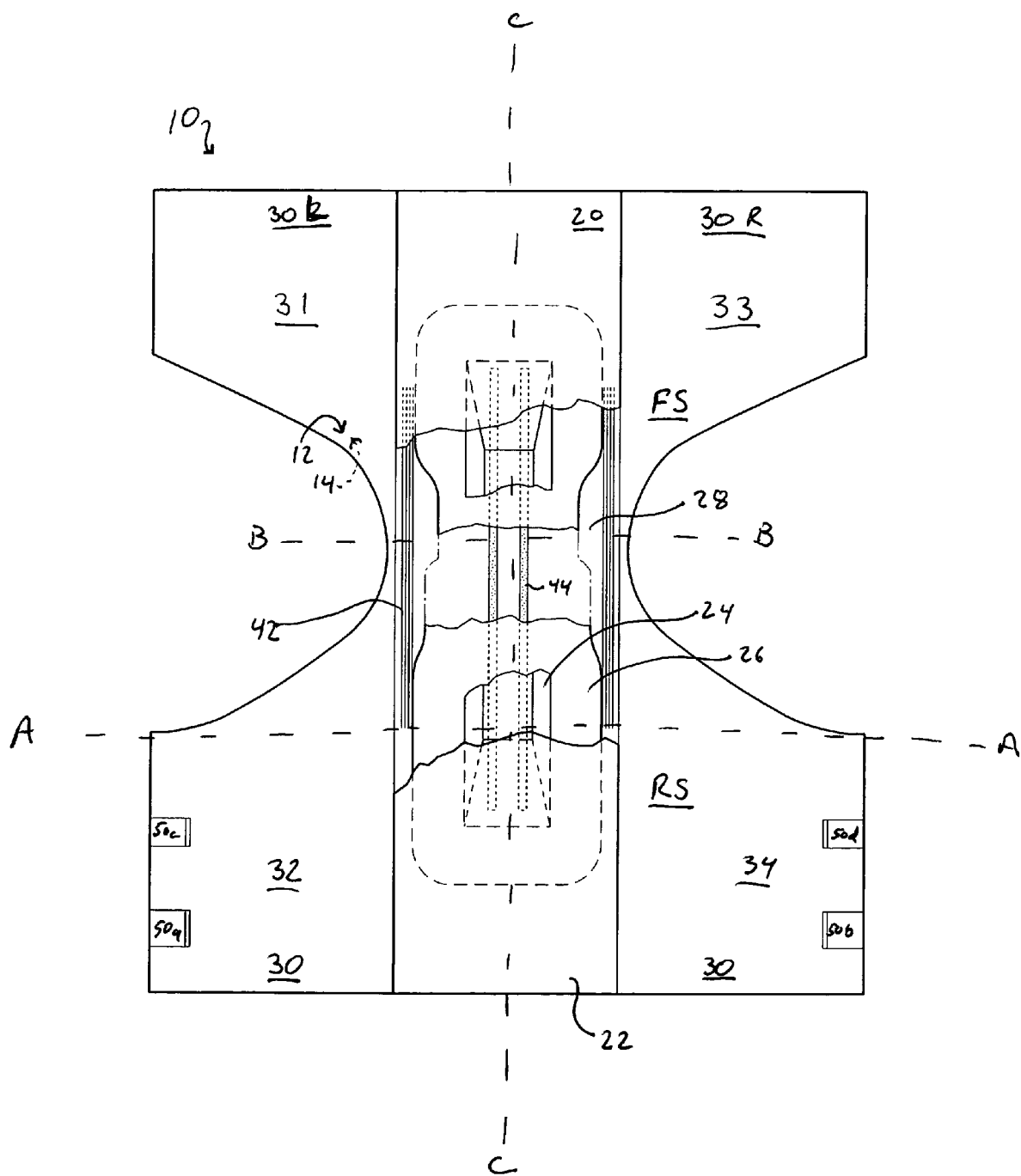
FIG. 1 is a perspective view of an embodiment of the absorbent article of the invention.

A preferred embodiment of an absorbent article of the present invention is the unitary disposable diaper 10, shown in FIG. 1. As used herein, the term "diaper" refers to an absorbent article generally worn by infants and incontinent persons that is worn about the lower torso of the wearer. It should be understood, however that the present invention is also applicable to other absorbent articles such as incontinent briefs, incontinent undergarments, training pants, diaper holders, and panty liners and other feminine hygiene products. In particular, training pants have side panels which are pre-attached whereas ordinary diapers have wings which are fastened together to secure the diaper.

FIG. 1 is a plan view of the diaper 10 of the present invention, with elastic induced contraction pulled out, with a portion of the structure cut away to reveal the inner construction of diaper 10, and with body-facing side 12 facing upwardly. Diaper 10 has a longitudinal axis defined by longitudinal centerline C, the term "longitudinal", as used herein, referring to a line, axis or direction in the plane of diaper 10 that is generally aligned with, or parallel to, longitudinal centerline C and defines the length of diaper 10. Transverse axis B extends through diaper 10, intersecting longitudinal centerline C at a right angle in the plane of diaper 10. Transverse axis B defines the transverse orientation relative to diaper 10 and divides diaper 10 into front and rear sections FS and RS respectively. As used herein, the term "transverse" refers to a line, axis or direction that is generally perpendicular to the longitudinal direction and defines the width of diaper 10.

The perimeter of Diaper 10 is defined by backsheet 30. The diaper 10 can be divided into three regions: a containment assembly 20 which extends symmetrically along longitudinal centerline C, and two longitudinally disposed portions 30L and 30R which extend variably in the transverse direction along their length and which define the left and right sides of the diaper respectively. In its preferred embodiment, backsheet 30 of diaper 10 has an "hourglass" configuration wherein portions 30L and 30R narrow to form a crotch region at transverse axis B between front and rear sections FS and RS.

Figure 2:
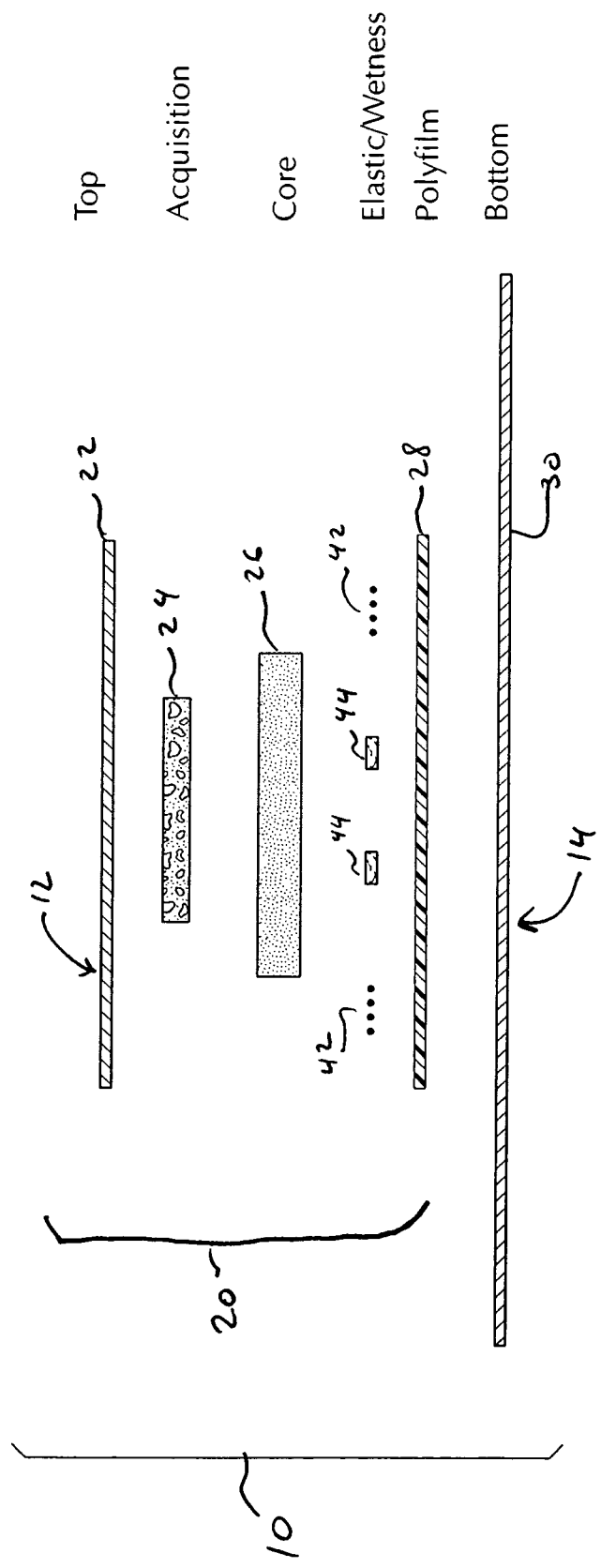
FIG. 2 is a lateral cross-sectional view of the absorbent article of FIG. 1.

Referring to FIGS. 1 and 2, the structure of diaper 10 is illustrated from body-facing surface 12 toward garment or outer surface 14. Containment assembly 20 preferably comprises a topsheet 22, an acquisition layer 24, an absorbent core 26 and a backing film 28. In a preferred embodiment, crotch elastic bands 42 and/or wetness indicators 44 may be added to one of the components of containment assembly 20. Containment assembly 20 is mounted upon backsheet 30 to form diaper 10.

Topsheet 22 may be made of any suitable relatively liquid-pervious material currently known in the art or later discovered that permits passage of a liquid therethrough. Examples of suitable top sheet materials include nonwoven, spunbonded or carded webs of polypropylene, polyethelene, nylon, polyester and blends of these materials perforated, apertured or reticulated films, and the like. Nonwoven materials are exemplary because such materials readily allow the passage of liquids to the underlying acquisition layer 24, and therethrough to absorbent core 26. The top sheet is preferably formed of a single ply of nonwoven material that may be made of thermally bonded, spunbonded fibers, spunbond-meltblown-spunbond or fibers that have been hydroentangled, having a basis weight of 10-30 grams per square meter and having appropriate strength and softness for use as a topsheet in an application which will be in contact with human skin. Topsheet 22 may be treated with surfactant, rendering it hydrophilic to facilitate the passage of moisture through topsheet 22 and into the interior of containment assembly 20. The present invention is not intended to be limited to any particular material for top sheet 24 and other top sheet materials will be readily apparent to those skilled in the art.

Acquisition layer 24 may be a single layer or multiple layers made of synthetic or natural material, or a combination of both, or a single multilayer apertured film. Acquisition layer 24 serves to quickly collect and distribute discharged body fluid to absorbent core 26. Because such fluid is typically discharged in gushes, the area of absorbent core 26 proximate to the point of fluid discharge may be overwhelmed by its rate, resulting in a leak. Therefore, the acquisition layer 24 facilitates transport of the fluid from the point of discharge across its surface area to contact other parts of absorbent core 26 from which it can be more readily absorbed. The use of an acquisition layer is well known in the art. Accordingly, acquisition layer 24 of diaper 10 of the present invention may have any well known or as yet undiscovered composition. Alternatively, absorbent core 26 may have the construction disclosed in U.S. Pat. No. 6,068,620 or U.S. Pat. No. 6,646,180 to Chmielewski, both of which are hereby incorporated by reference.

Absorbent core 26 may be any absorbent material which is generally compressible, conformable to the shape of the wearer's body and will not impede normal movement by the wearer, and capable of absorbing and retaining liquids such as urine and certain other body exudates. The absorbent core 26 may be manufactured in a wide variety of sizes and shapes, (e.g., rectangular, hourglass, "T"-shaped, asymmetric, etc.) and from a wide variety of liquid-absorbent materials commonly used in disposable diapers and other absorbent articles such as wood pulp fluff. Examples of other suitable absorbent materials include creped cellulose wadding; meltblown polymers; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of absorbent core 26 may also be varied (e.g., the absorbent core may have varying caliper zones, a hydrophilic gradient, an absorbent gelling material gradient, or lower average density and lower average basis weight acquisition zones; or may comprise one or more layers or structures, i.e., members, including sheets or webs. In addition, each member need not be formed of a single unitary piece of material, but may be formed of a number of smaller strips or components joined together lengthwise or width-wise, as long as they are in fluid communication with one another.) The total absorbent capacity of absorbent core 26 should, however, be compatible with the design loading and the intended use of the diaper 10. Further, the size and absorbent capacity of the absorbent core 26 may be varied to accommodate wearers ranging from infants through adults.

Backing film 28 preferably is made from any suitably pliable liquid impervious material known in the art. Typical backing film materials include films of polyethylene, polypropylene, polyester, nylon and polyvinyl chloride and blends of these materials. For example, backing film 28 can be made of a polyethylene film having a thickness in the range of 0.5 to 2.0 mils. Other backing film materials will be readily apparent to those skilled in the art. Backing film 28 preferably has sufficient liquid imperviousness to prevent any leakage of fluids. The required level of liquid imperviousness may vary between different locations on diaper 10. Accordingly, the backing film 28 may be made vapor pervious or multi layered, having varying degrees of liquid-imperviousness. Backing film 28 may have the same width as topsheet 22, or may be narrower or wider. Preferably, topsheet 22 and backing film 28 have about the same widths.

As discussed above, Topsheet 22, acquisition layer 24, absorbent core 26 and backing film 28 form the basic components necessary to the preferred embodiment of containment assembly 20. Crotch elastic bands 42 may be adhered to the lateral margins of containment assembly 20 to bias containment assembly 20 into a shape which conforms to that of the wearer's body. Furthermore, wetness indicators 44 may be provided in contact with absorbent core 26 to provide a visual indication that diaper 10 has received and is holding liquid.

Containment assembly 20 may be self contained, for example by adhering the perimeter of topsheet 22 to the perimeter of backing film 28, such as with ordinary adhesive, or by bonding, with heat or ultrasonically, the components to each other. In such a construction, acquisition layer 24 and absorbent core 26 are contained within a package formed by backing film 28 and topsheet 22. Containment assembly 20 may then adhered to backsheet 30. Alternatively, topsheet 22 may be adhered directly to backsheet 30, topsheet 22 securing the components of containment assembly 20 between backsheet 30 and topsheet 22. Although the precise shape of containment assembly 20 may vary, it is preferred that top sheet 22 and backing film 28 have generally the same shape and dimensions. Particularly, however, backing film 28 should be sufficiently large to at least completely cover the outer surface of absorbent core 26 to prevent leakage of fluid from absorbent core 26 to backsheet 30, but must not significantly exceed the width of topsheet 22, and should generally be slightly narrower than topsheet 22.

Backsheet 30 is made of a liquid and/or vapor-pervious material which may be selected from the same group of materials from which the top sheet was selected and preferably having a weight of between 5-45 grams per square meter. Unlike topsheet 22, however, the material used for backsheet 30 is preferably rendered hydrophobic by omitting the surfactant discussed above with respect to topsheet 22. Backsheet 30 may be manufactured by well known methods such as thermal bonding, chemical bonding, spun bonding and hydroentanglement, or by a combination of spun bonding and hydroentanglement. A spun bonded nonwoven that is post treated by post bonding Backsheet 30 preferably has the same or greater longitudinal dimension to that of containment assembly 20. As discussed below, however, it is critical that backsheet 30 be formed of a single layer of material, and that the lateral dimension of the backsheet exceed, at least in part, the width of containment assembly 20.

As shown in FIG. 1, containment assembly 20 is preferably attached to backsheet 30 symmetrically along longitudinal centerline C. As containment assembly 20 is necessarily narrower and preferably shorter than at least some portions of backsheet 30, portions of backsheet 30 remain unattached from containment assembly 20. In the preferred embodiment, the hourglass shape of backsheet 30 results in two wings in each of longitudinal portions L and R to which containment assembly 20 is not attached.

Alternatively, a T-shaped backsheet would result in one such wing in each of L and R respectively. Wings 31 and 33 are on front section FS of diaper 10 and wings 32 and 34 on rear section RS thereof. As each of wings 31-34 are formed of marginal portions of backsheet 30, they comprise a single layer of liquid and vapor pervious material, rear wings 32 and 34 being provided with fasteners 50a-50d. The fasteners may be any of adhesive, hook-and-loop, loopless or any other fastener known in the art which is capable of securing itself, preferably removably, to the material of backsheet 30. Fasteners 50a-50d may also be double-sided patches attached to backsheet 30 on one side and having a fastening material on the other.

It is known in the art to provide fasteners which have one end coated with a pressure sensitive adhesive. In a case where fasteners 50a-50d are formed of such pressure adhesive material, landing zones (not shown) are provided on the opposite side of the diaper corresponding to the location at which the fasteners are expected to be attached during assembly of the diaper. In this case, the landing zones may be a coated release paper or similarly smooth surface disposed over the nonwoven backsheet 30. Similarly, a hook-and-loop type arrangement requires fasteners 50a-50d to have a plurality of either hooks or loops disposed on one side thereof, with a landing zones providing corresponding loops or hooks located respectively in corresponding regions on the opposite side of the diaper. The need for landing zones is a result of the fact that nonwoven material may not form a sufficiently strong bond with adhesive or other conventional fasteners to support the assembled diaper during use.

The need to provide a landing zone has been eliminated, however, by the introduction of minihook fasteners which are capable of fastening securely to conventional nonwovens without a corresponding landing zone. These loopless fasteners are ideal for providing a degree of flexibility and choice to the user in the positioning of the fasteners on the diaper.

A problem recognized with the loopless fastener, however, is that the flexibility they provide encourage the use of inappropriately sized diapers, for example a large diaper on a medium sized person, with the fasteners merely being secured to a more remote portion of the nonwoven outer surface of the diaper. This type of misuse is wasteful and could not occur in diapers requiring a landing zone as the landing zones limit the areas on the diaper to which a fastener can be applied.

To ameliorate this type of misuse, a stay away zone 100 could be provided on a portion of the outer surface of the diaper. The stay away zone could be limited to the most remote areas, thereby permitting a wide range of fastener placement while preventing improper sizing of the diaper.

Stay away zone 100 can be created by spraying a solution or attaching a film over a portion of nonwoven backsheet 30 to which the fastener could not attach. Alternately, a stay away zone could be defined by selectively modifying areas of nonwoven backsheet 30, such as by heat or compression, to destroy its ability to adhere to the hooks of a loopless fastener. For example, a patch having dimensions of 7 inches×11 inches and made from stay away zone material may be attached to the outer surface of the front of the diaper to prevent misuse.

Figure 3:
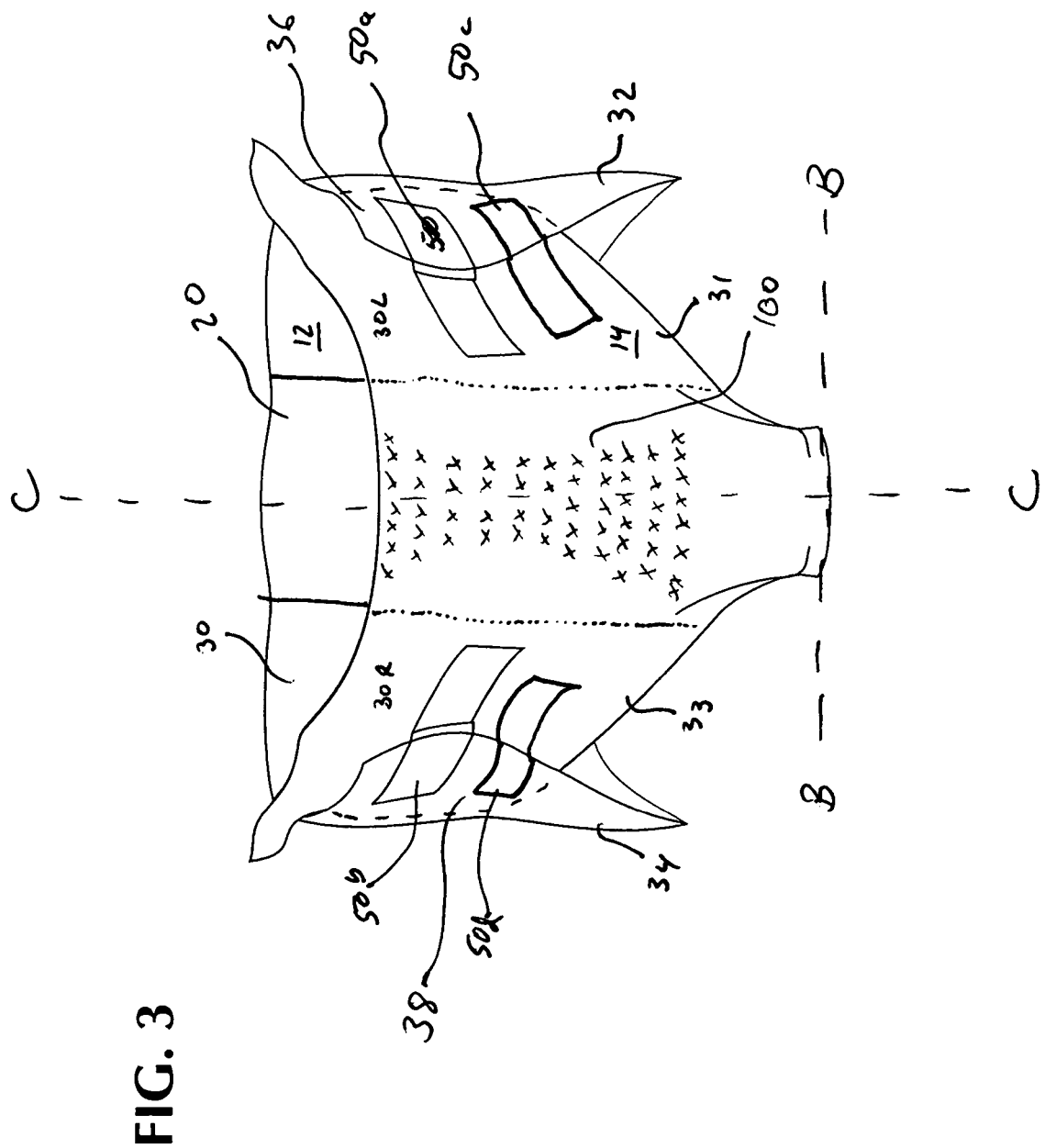
FIG. 3 is a perspective view of the absorbent article of the invention assembled for use.

As shown in FIG. 3, diaper 10 is shown as assembled. The diaper 10 is folded about lateral axis B as it would be about a wearer, such that body facing side 12 is oriented inward and outer surface 14 is oriented outward. Containment assembly 20 is shown between left and right longitudinal portions L and R which define the breathable portions of diaper 10 respectively. Specifically, on the left, wing 32 is shown folded over wing 31 and fastened thereto by fasteners 50a and 50c, creating overlapping region 36. Similarly, wing 34 is shown folded over wing 33 and fastened thereto by fasteners 50b and 50d, creating overlapping region 38. Thus, at the regions of diaper 10 defined by longitudinal portions L and R, only a single layer of liquid and vapor permeable material contact the skin of the wearer, with the exception of overlapping regions 36 and 38, which are similarly permeable. Thus, a diaper 10 is provided having breathable sides which increase the comfort of the diaper to the wearer.

Additionally, due to the reduced size of impervious backing film 28 relative to backsheet 30, a reduced amount of film material is required in the construction of diaper 10 relative to a diaper having an impervious backsheet. As backing film 28 is typically plastic and therefore non-biodegradable, the present invention provides a diaper with a minimum of such material.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:

a backsheet consisting of a single, vapor pervious layer having a shape defining a longitudinal axis, a minimum lateral dimension and a maximum lateral dimension, said backsheet defining a front region at one end of said longitudinal axis and a rear region at the other end of said longitudinal axis, and a crotch region joining said front and rear regions, wherein said front and rear regions have a lateral dimension of approximately said maximum lateral dimension, and said crotch region has a lateral dimension of approximately said minimum lateral dimension;

one or more fasteners, each of said fasteners attached at one end to a first part of said backsheet and having a fastening material at a second end thereof, said fastening material adapted to removably engage a substantial portion of said backsheet; and a containment assembly having a shape defining a maximum lateral dimension which is less than the maximum lateral dimension of said backsheet, said containment assembly comprising;
a vapor pervious topsheet;
a vapor impervious backing film disposed beneath said topsheet; and
an absorbent core sandwiched between said topsheet and said backing film; wherein
said containment assembly is attached to said backsheet along said longitudinal axis, said backsheet forming a plurality of breathable regions each consisting of a single layer laterally disposed beyond said containment assembly, at least a portion of said backsheet being altered to completely resist engagement by said fastening material so that said fastener is capable of engaging only said substantial portion of said backsheet and said at least a portion of said backsheet forms a stay-away zone to which said fastening material is not capable of attaching, wherein the stay-away zone is disposed within at least one of the front and back regions and a maximum lateral dimension of the stay-away zone does not extend beyond the minimum lateral dimension of the backsheet.

2. The absorbent article of claim 1, wherein said shape of said containment assembly is generally symmetrical about a longitudinal axis.

3. The absorbent article of claim 2 wherein said topsheet of said containment assembly is attached to said backsheet, and said absorbent core and said backing film are positioned between said topsheet and said backsheet.

4. The absorbent article of claim 2 wherein said topsheet of said containment assembly is attached to at least a portion of said backing film.

5. The absorbent article of claim 2 wherein said containment assembly incorporates absorbent members to assist in the placement of said absorbent article against the body of a wearer.

6. The absorbent article of claim 2 wherein an acquisition layer is positioned between said topsheet and said absorbent core to facilitate distribution of moisture across said absorbent core.

7. The absorbent article of claim 1 wherein said laterally disposed breathable regions are provided with fasteners for securing said absorbent article to the body of a wearer.

8. The absorbent article of claim 7 wherein said backsheet is formed of a spunbond nonwoven and said fasteners are removably attachable thereto without adhesive.

9. The absorbent article of claim 1 wherein said maximum lateral dimension of said containment assembly does not exceed the minimum lateral dimension of said backsheet.

10. The absorbent article of claim 1 wherein said fastening material is adapted to engage a landing zone attached to said second part of said backsheet, said landing zone comprising a different material from that of said backsheet.

11. The absorbent article of claim 10 wherein said backsheet is formed of a nonwoven material, and said fastening material resists direct engagement with said nonwoven material.

12. The absorbent article of claim 1 wherein said fastening material is a pressure sensitive adhesive.

13. The absorbent article of claim 10 wherein said fastening material is a first part of a two-part fastener, said landing zone comprising a second part of a two-part fastener.

14. The absorbent article of claim 1 wherein said backsheet is formed of nonwoven material and said fastening material is adapted to directly engage nonwoven material.

15. The absorbent article of claim 14 wherein said backsheet is formed of a hydroentangled, spunbond nonwoven.

16. The absorbent article of claim 14 wherein said backsheet is a spunbond nonwoven.

17. The absorbent article of claim 14 wherein at least a portion of said backsheet is covered by a material that resists engagement by said fastening material.

18. A unitary disposable diaper having breathable side panels comprising:
a backsheet consisting of a single layer having a longitudinal axis defining a front portion at a first end of said longitudinal axis and a rear portion at a second end of said longitudinal axis connected by a crotch portion between said front portion and said rear portion, said backsheet having a maximum lateral dimension at each of said front and rear portions thereof and having a minimum lateral dimension at said crotch region;
one or more fasteners, each of said fasteners attached at one end to a first part of said backsheet and having a fastening material at a second end thereof, said fastening material adapted to removably engage a substantial portion of said backsheet; and
a containment assembly having a shape defining a maximum lateral dimension which is less than the maximum lateral dimension of said backsheet, said containment assembly comprising;
a vapor pervious topsheet;
a vapor impervious backing film disposed beneath said topsheet; and
an absorbent core sandwiched between said topsheet and said backing film;
wherein said containment assembly is attached to said backsheet such that the containment assembly does not extend laterally beyond the backsheet, said backsheet forming a plurality of breathable regions each consisting of a single layer laterally disposed beyond said containment assembly, said breathable regions fastenable to each other to form said breathable side panels, at least a portion of said backsheet being altered to completely resist engagement by said fastening material so that said fastener is capable of engaging only said substantial portion of said backsheet and said at least a portion of said backsheet forms a stay-away zone to which said fastening material is not capable of attaching, wherein the stay-away zone is disposed within at least one of the front and back portions and a maximum lateral dimension of the stay-away zone does not extend beyond the minimum lateral dimension of the backsheet.

19. The unitary disposable diaper of claim 18 wherein said fastening material is adapted to engage a landing zone attached to said second part of said backsheet, said landing zone comprising a different material from that of said backsheet.

20. The unitary disposable diaper of claim 19 wherein said backsheet is formed of a nonwoven material, and said fastening material resists direct engagement with said nonwoven material.

21. The unitary disposable diaper of claim 19 wherein said fastening material is a pressure sensitive adhesive.

22. The unitary disposable diaper of claim 18 wherein said fastening material is a first part of a two-part fastener, said landing zone comprising a second part of a two-part fastener.

23. The unitary disposable diaper of claim 18 wherein said backsheet is formed of nonwoven material and said fastening material is adapted to directly engage nonwoven material.

24. The unitary disposable diaper of claim 23 wherein said backsheet is formed of a hydroentangled, spunbond nonwoven.

25. The unitary disposable diaper of claim 23 wherein said backsheet is a spunbond nonwoven.

26. The unitary disposable diaper of claim 23 wherein at least a portion of said backsheet is altered to resist engagement by said fastening material.

27. The unitary disposable diaper of claim 23 wherein at least a portion of said backsheet is covered by a material that resists engagement by said fastening material.

28. The unitary disposable diaper of claim 18 wherein said backsheet is formed of a single layer of spunbond nonwoven material.

29. The unitary disposable diaper of claim 18 wherein said containment assembly is generally rectangular, having a longitudinal dimension approximately equal in length to said longitudinal axis.

30. The absorbent article of claim 29 wherein said topsheet has a lateral dimension slightly wider than that of said backing film, wherein said topsheet is attached to said backsheet, said absorbent core and said backing film positioned therebetween.

31. The absorbent article of claim 18 wherein said backing film is attached to said backsheet.

32. The absorbent article of claim 18 wherein said backing film is composed of a plurality of layers of vapor permeable material.

33. The absorbent article of claim 18 wherein said backing film is perforated.

34. An absorbent article comprising:
- a single-layer, vapor pervious backsheet having a shape defining a longitudinal axis, a minimum lateral dimension and a maximum lateral dimension, said backsheet defining a front region at one end of said longitudinal axis and a rear region at the other end of said longitudinal axis, and a crotch region joining said front and rear regions, wherein said front and rear regions have a lateral dimension of approximately said maximum lateral dimension, and said crotch region has a lateral dimension of approximately said minimum lateral dimension;
- one or more fasteners, each of said fasteners attached at one end to a first part of said backsheet and having a fastening material at a second end thereof, said fastening material adapted to removably engage a substantial portion of said backsheet; and
- a containment assembly having a shape defining a maximum lateral dimension which is less than the maximum lateral dimension of said backsheet, said containment assembly comprising;
  - a vapor pervious topsheet;
  - a vapor impervious backing film disposed beneath said topsheet; and
  - an absorbent core sandwiched between said topsheet and said backing film; wherein
- said containment assembly is attached to said backsheet along said longitudinal axis, said backsheet forming a plurality of breathable regions laterally disposed beyond said containment assembly, at least a portion of said backsheet being altered to completely resist engagement by said fastening material so that said fastener is capable of engaging only said substantial portion of said backsheet and said at least a portion of said backsheet forms a stay-away zone to which said fastening material is not capable of attaching, wherein the stay-away zone is disposed within at least one of the front and back regions and extends substantially across the minimum lateral dimension of the backsheet.

* * * * *